US007267981B2

(12) United States Patent
Amit et al.

(10) Patent No.: US 7,267,981 B2
(45) Date of Patent: Sep. 11, 2007

(54) HUMAN FORESKIN FIBROBLASTS FOR CULTURING ES CELLS

(75) Inventors: Michal Amit, Misgav (IL); Joseph Itskovitz-Eldor, Haifa (IL)

(73) Assignee: Technion Research & Development Foundation Ltd., Haifa (IL)

( * ) Notice: Subject to any disclaimer, the term of this patent is extended or adjusted under 35 U.S.C. 154(b) by 330 days.

(21) Appl. No.: 10/368,045

(22) Filed: Feb. 19, 2003

(65) Prior Publication Data

US 2004/0067580 A1 Apr. 8, 2004

Related U.S. Application Data

(60) Provisional application No. 60/416,242, filed on Oct. 7, 2002.

(51) Int. Cl.
*C12N 5/00* (2006.01)
*C12N 5/02* (2006.01)
*C12N 5/08* (2006.01)

(52) U.S. Cl. .................. 435/373; 435/325; 435/366; 435/375; 435/377

(58) Field of Classification Search ............. 435/325, 435/366, 377, 373, 375
See application file for complete search history.

(56) References Cited

U.S. PATENT DOCUMENTS

| 4,460,574 A | * | 7/1984 | Yabrov ............... 424/85.6 |
| 6,200,806 B1 | | 3/2001 | Thomson |
| 2002/0072117 A1 | | 6/2002 | Xu et al. |

FOREIGN PATENT DOCUMENTS

| WO | WO99/20741 | 4/1999 |
| WO | WO 2004/055155 | 1/2004 |

OTHER PUBLICATIONS

Zipori et al. In Vitro Formation of Stromal Cells from Human and Mouse Bone Marrow. Experiment. Hematol. 1985, vol. 13, pp. 603-609.*
Amit et al, "Clonally Derived Human Embryonic Stem Cell Lines Maintain Pluripotency and Proliferative Potential for Prolonged Periods of Culture", *Developmental Biology*, 227(2):271-278, 2000.
Thomson et al, "Isolation of a Primate Embryonoc Stem Cell Line", *Proc. Natl. Acad. Sci. USA*, 92:7844-7848, 1995.
Richards et al, "Human Feders Support Prolonged Undifferentiated Growth of Human Inner Cell Masses and Embryonic Stem Cells", *Nature*, 20:933-936, 2002.
Amit et al, "Derivation and Spontaneous Differentiation of Human Embryonic Stem Cells", *J. Anat.*, 200:225-232, 2002.
Sreinert et al, "Transient expression of human telomerase extends the life span of normal human fibroblasts", *Biochem Biophys Res Commun.* Jul. 14, 2000;273(3):1095-8.
Strojek et al, "A Method for Cultivating Morphologically Undifferated Embryonic Stem Cells from Porcine Blastocytes", *Theriogenology*, 33(4):901-913, 1990.
Bruns et al, "Type VI collagen in extracellular, 100-nm periodic filaments and fibrils: identification by immunoelectron microscopy", *J Cell Biol.* Aug. 1986;103(2):393-404.
Yoshizawa et al, "Testosterone and insulin-like growth factor (IGF) I interact in controlling IGF-binding protein production in androgen-responsive foreskin fibroblasts", *J Clin Endocrinol Metab.* Apr. 2000;85(4):1627-33.
Waelti et al, "Co-Culture of Human Keratinicytes on Post-Mitotic Human Dermal Fibroblast Feeder Cells: Production of Large Amounts of Interleukin6", *J. Invest. Dermatol.*, 98:805-808, 1992.
Grigoriev et al, "Senescent fibroblasts as feeder cells for lymphoid cell cloning", *Anal Biochem.* May 1, 1996;236(2):250-4.
Richards et al. "Comparative Evaluation of Various Human Feeders for Prolonged Undifferentiated Growth of Human Embryonic Stem Cells", *Stem Cells*, 21: 546-556, 2003.
Amit et al. "Human Feeders Layers for Human Embryonic Stem Cells", *Biology of Reproduction*, 68: 2150-2156, 2003.
Hovatta et al. "A Culture System Using Human Foreskin Fibroblasts as Feeder Cells Allows Production of Human Embryonic Stem Cells", *Human Reproduction*, 18(7): 1404-1409, 2003.
Howell et al. "Elimination of Mycoplasma From Human B-Lymphoblastoid Cell Lines", *Human Immunology*, 5(3): 233-238, 1982.
Matic et al. "Basal Foreskin Keratinocytes That Lack Expression of Connexin 43 Exhibit Stem Cell Characteristics", *Molecular Biology of the Cell*, 10(Suppl.)204: 35a, 1999. & 39th Annual Meeting of the American Society for Cell Biology, Washington, D.C., Dec. 11-15, 1999.
Limat et al. "Post-Mitotic Human Dermal Fibroblasts Efficiently Support the Growth of Human Follicular Keratinocytes", *Journal of Investigative Dermatology*, 92(5): 758-762, 1989.
Muggleton-Harris et al. "Replicative Potential of Individual Cell Hybrids Derived From Young and Old Donor Human Skin Fibroblasts", *Somatic Cell Genetics*, 8(1): 41-50, 1982.

* cited by examiner

*Primary Examiner*—Deborah Crouch

(57) ABSTRACT

A cell culture comprising human foreskin cells, the human foreskin cells being capable of maintaining stem cells in an undifferentiated state when co-cultured therewith.

16 Claims, 6 Drawing Sheets
(3 of 6 Drawing Sheet(s) Filed in Color)

HUMAN FORESKIN FIBROBLASTS FOR CULTURING ES CELLS

This application claims the benefit of priority from U.S. Provisional Patent Application No. 60/416,242, filed Oct. 7, 2002.

FIELD AND BACKGROUND OF THE INVENTION

The present invention relates to human foreskin cells, which are capable of maintaining stem cells in an undifferentiated state in culture.

Embryonic stem (ES) cells are derived from the inner cell mass (ICM) of the mammalian blastocyst (Evans & Kaufman 1981; Martin 1981). These cells are pluripotent thus capable of developing into any organ or tissue type and even a complete embryo. When cultured in suspension ES cells aggregate and differentiate into simple embryoid bodies (EBs), however once cultured under suitable conditions (as further described hereinbelow), true ES cells are capable of indefinite proliferation in vitro in an undifferentiated state; maintaining a normal karyotype through prolonged culture; and maintaining the potential to differentiate to derivatives of all three embryonic germ layers (i.e., mesoderm, ectoderm and endoderm).

Mouse embryonic stem cells provide a powerful tool for introducing specific genetic changes into the mouse germ line.

Mouse ES cells combined into chimeras with normal preimplantation embryos and returned to the uterus participate in normal embryonal development [Richards (1994) Cytogenet. Cell Genet. 65: 169-171]. The ability of mouse ES cells to contribute to functional germ cell in chimeras provides a method for introducing site specific mutations into mouse lines. For example, with appropriate transfection and selection strategies, homologous recombination can be used to derive ES cell lines with planned alterations of specific genes. The genetically altered cells can be used to form chimeras with normal embryos and chimeric animals are recovered. Once ES cells contribute to the germ line in the chimeric animal, it is feasible to establish a mouse line for the planned mutation in the next generation. Thus, mouse ES cells provide refined mutagenesis screen that greatly accelerate functional mouse genomics and generate mammalian models for developmental processes and disease (Mills and Bradley, 2001).

Although mouse ES cells facilitate the understanding of developmental processes and genetic diseases, significant differences in primates and mouse development limit the use of mouse ES cells as a model of human development. Mouse and primate embryos differ significantly in temporal expression of embryonic genes, such as in the formation of the egg cylinder versus the embryonic disc [Kaufman, The Atlas of Mouse Development; London; Academic Press (1992)]; in the proposed derivation of some early lineages [O'Rahilly and Muller; Developmental Stages in Human Embryos, Washington; Carnegie Institution of Washington (1987)]; in the structure and function of the extraembryonic membranes and placenta [Mossman, Vertebrate Fetal Membranes; New Bruswick; Rutgers (1987)]; in growth factor requirement for development (e.g., the hematopoietic system) [Lapidot Lab. An. Sci. 43:147-149 (1994)]; and in adult structure and function (e.g., central nervous system).

Thus, to better reflect developmental differences, ES cells have also been generated from primates (Thomson et al., 1995, 1996, 1998).

Human ES cells offer insight into developmental events, which cannot be studied directly in the intact human embryo. For example, in the early post-implantation period, knowledge of normal human development is largely restricted to the description of a limited number of sectioned embryos and to analogies drawn from experimental embryology of other species.

Furthermore, screens based on the in vitro differentiation of human ES cells to specific lineages can identify gene targets, which can be used for the design and configuration of tissue regeneration therapies and teratogenic or toxic compounds.

For example, Parkinson's disease and juvenile-onset diabetes mellitus, result from the death or dysfunction of one or several cell types. Replacement of non-functional cells using ES cells technology can offer a lifelong treatment.

In order to maintain human ES cells in an undifferentiated state ES culture must be supplemented with factors which maintain cell proliferation, inhibit ES cell differentiation and preserve pluripotency. Current methods for culturing ES cells include the use of mouse feeder cells or conditioned medium. Other methods aim to provide an animal-free environment for the growth of human ES cells.

Animal Based Cultures

Animal based cultures include mouse feeder layers supplemented with serum or serum replacement and mouse originated matrices supplemented with conditioned medium.

Mouse Feeder Layers

The most common method for culturing ES cells is based on mouse embryonic fibroblasts (MEF) as a feeder cell layer supplemented with tissue culture medium containing serum or leukemia inhibitor factor (LIF) which supports the proliferation and the pluripotency of the ES cells (Thomson et al, 1998; Reubinoff et al 2000). MEF cells are derived from day 12-13 mouse embryos in medium supplemented with fetal bovine serum. Under these conditions ES cells can be maintained for many passages in culture while preserving their phenotypical and functional characteristics. However, unlike mouse ES cells, the presence of exogenously added LIF does not prevent differentiation of the human ES cells. Furthermore, the use of feeder cells substantially increases the cost of production, and makes scale-up of human ES cell culture impractical. Additionally, the feeder cells are metabolically inactivated to keep them from outgrowing the stem cells, hence it is necessary to have fresh feeder cells for each splitting of the human ES culture. Procedures are not yet developed for completely separating feeder cell components away from embryonic cells prepared in bulk culture. Thus, the presence of xenogeneic components from the feeder cells complicates their potential use in human therapy.

ES cells can also be cultured on MEF under serum-free conditions using serum replacement supplemented with basic fibroblast growth factor (bFGF) (Amit et al., 2000). Under these conditions the cloning efficiency of ES cells is 4 times higher than under fetal bovine serum. In addition, following 6 months of culturing under serum replacement the ES cells still maintain their pluripotency as indicated by their ability to form teratomas which contain all three embryonic germ layers. Although this system uses a better-defined culture conditions, the presence of mouse cells in the culture exposes the human culture to pathogens which restricts their use in cell-based therapy.

Conditioned Medium

ES cells can also be cultured in a feeder-free environment. Stem cells are grown on a solid surface such as an extracellular matrix (e.g., Matrigel®™ or laminin) in the presence of culture medium. The culture medium used for growing the stem cells contains factors that effectively inhibit differentiation and promote their growth such as MEF-conditioned medium and bFGF. However, this culturing method is limited by the high costs of both the matrix and the production of MEF conditioned medium. In addition, both the matrix and the conditioned medium consist of mouse material, which is basically inconsistent in terms of composition.

However, the major disadvantage of all the abovementioned animal-based xenosupport systems (i.e., MEF with serum and serum replacement, extracellular matrices and conditioned medium) is that they present the risk of animal pathogen cross-transfer to the human ES cells, thus compromising future clinical application.

Animal-Free Cultures

Animal free cultures provide a pathogen-free environment for the growth of ES cells. These cultures rely on human feeder layers supplemented with human serum or serum replacement suitable for the growth of human stem cells.

Human Feeder Layer

Human ES cells can be grown and maintained using human embryonic fibroblasts or adult fallopian epithelial cells. When grown on human feeder cells the human ES cells exhibit normal karyotypes, present alkaline phosphatase activity, express Oct-4 and other embryonic cell surface markers including SSEA-3, SSEA-4, TRA-1-60, and GCTM-2, form teratomas in vivo, and retain all key morphological characteristics (Richards et al 2002). However, the major disadvantage of using human embryonic fibroblasts or adult fallopian tube epithelial cells as feeder cells is that both of these cell lines have a limited passage ability of only 8-10 times, thereby limiting the ability of a prolonged ES growth period. For a prolonged culturing period, the ES cells must be grown on human feeder cells originated from several subjects which results in an increased variability in culture medium.

There is thus a widely recognized need for, and it would be highly advantageous to have, an animal-free culturing system, capable of supporting stem cell proliferation in culture for extended periods of time, while maintaining their undifferentiated state, devoid of the above limitations.

SUMMARY OF THE INVENTION

According to one aspect of the present invention there is provided a cell culture comprising human foreskin cells, the human foreskin cells being capable of maintaining stem cells in an undifferentiated state when co-cultured therewith.

According to further features in preferred embodiments of the invention described below, the human foreskin cells are capable of forming a mono-layer in the cell culture.

According to still further features in the described preferred embodiments the stem cells are of embryonic origin.

According to still further features in the described preferred embodiments the stem cells are of human origin.

According to still further features in the described preferred embodiments the cell culture includes a culture medium including serum and/or serum replacement.

According to still further features in the described preferred embodiments the serum is provided at a concentration of at least 10%.

According to still further features in the described preferred embodiments the serum replacement is provided at a concentration of at least 15%.

According to still further features in the described preferred embodiments the serum is human serum.

According to still further features in the described preferred embodiments the serum is provided at a concentration of 20%.

According to still further features in the described preferred embodiments the serum replacement is provided at a concentration of 30%.

According to another aspect of the present invention there is provided a method of maintaining stem cells in an undifferentiated state comprising co-culturing the stem cells with a human foreskin feeder cell line.

According to yet another aspect of the present invention there is provided a cell culture comprising: (i) stem cells; and (ii) human foreskin cells capable of maintaining the stem cells in an undifferentiated state.

According to still further features in the described preferred embodiments, the human foreskin feeder cell line is prepared by: (a) isolating foreskin cells from foreskin tissue; (b) culturing the foreskin cells in a culture medium including serum and/or serum replacement thereby preparing the human foreskin feeder cell line.

According to still further features in the described preferred embodiments the foreskin tissue is obtained from an 8-14 day old male individual.

According to still further features in the described preferred embodiments isolating foreskin cells from foreskin tissue is effected by: (i) mincing the foreskin tissue; (ii) dissociating the foreskin tissue resultant from step (i) into single cells.

According to still further features in the described preferred embodiments dissociating the foreskin tissue is effected via treatment with trypsin.

According to still further features in the described preferred embodiments the serum and/or serum replacement are provided at a concentration of at least 10%.

According to still further features in the described preferred embodiments the serum and/or serum replacement are provided at a concentration of 15%.

According to still further features in the described preferred embodiments the human foreskin cells of the culture maintain the stem cells in an undifferentiated, proliferative state through more than 87 passages.

According to still another aspect of the present invention there is provided a composition suitable for maintaining stem cells in an undifferentiated state, the composition comprising human foreskin cell conditioned medium.

According to still further features in the described preferred embodiments the composition further including a factor selected from the group consisting of a growth factor, an anti oxidant and an amino acid.

According to an additional aspect of the present invention there is provided a method of producing a conditioned medium suitable for maintaining stem cells in an undifferentiated state, the method comprising: (a) culturing human foreskin cells in a growth medium under conditions suitable for producing the conditioned medium; and (b) collecting the growth medium to thereby produce the conditioned medium suitable for maintaining stem cells in an undifferentiated state.

According to still further features in the described preferred embodiments the method of producing a conditioned medium further includes validating the ability of the conditioned medium to maintain the stem cells in an undifferentiated state following step (b), whereas validating is effected by a differentiation assay selected from the group consisting of morphology analysis, karyotype analysis and surface marker analysis.

The present invention successfully addresses the shortcomings of the presently known configurations by providing cell cultures and methods for propagating and maintaining stem cells in an undifferentiated state and in an animal-free environment.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the patent specification, including definitions, will control. In addition, the materials, methods, and examples are illustrative only and not intended to be limiting.

BRIEF DESCRIPTION OF THE DRAWINGS

The file of this patent contains at least one drawing executed in color photograph. Copies of this patent with color photograph(s) will be provided by the Patent and Trademark Office upon request and payment of necessary fee.

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

Figures 1A, 1B:
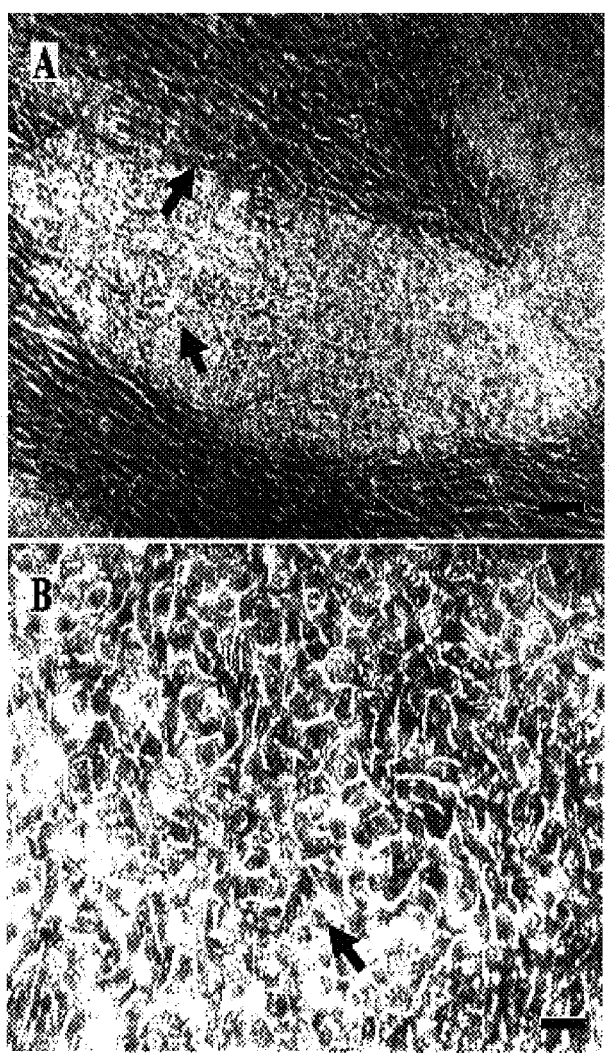

FIGS. 1a-b are photomicrographs depicting human ES cells grown on a foreskin feeder layer. FIG. 1a is a photomicrograph of a human ES cell colony (line I-6) grown for 61 consecutive passages on foreskin feeder layers. Note that the colony is organized in a long and elliptic manner. Size bar represents 100 µM. FIG. 1b is a photomicrograph of individual human ES cells (line I-3) grown for 37 consecutive passages on foreskin feeder layers. Note that the cells retain their typical ES cell morphology, i.e. high nucleus to cytoplasm ratio, presence of nucleoli and intercellular gaps. Size bar represents 38 µM.

Figure 2A:
Figure 2B:
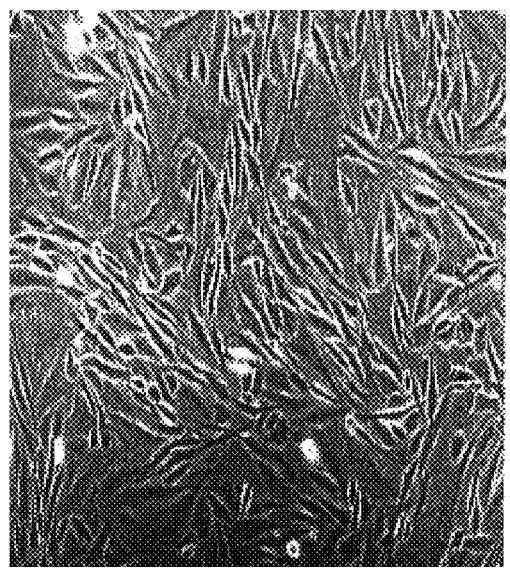

FIGS. 2a-b are photomicrographs of MEF and foreskin cells cultured for 4 days in the presence of 100 µg/ml Neomycin. Note the cell death and the abnormal phenotype of the MEF culture (FIG. 2a, size bar represents 40 µm) as compared with the normal cell phenotype of the F-3 foreskin culture (FIG. 2b, size bar represents 100 µm).

Figure 3A:
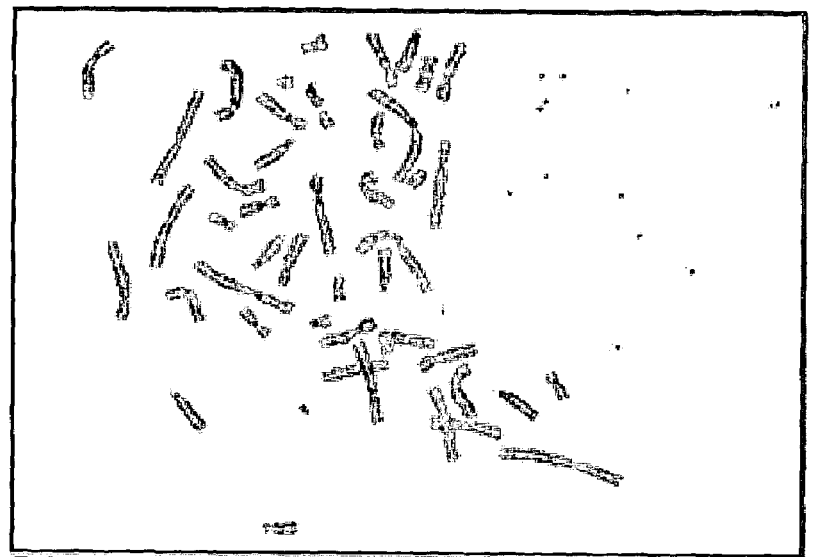

FIG. 3a is a photomicrograph depicting G-banding metaphase of ES cells (line I-3) following 29 passages on foreskin feeder layers which have been grown for 107 passages following their derivation.

Figure 3B:
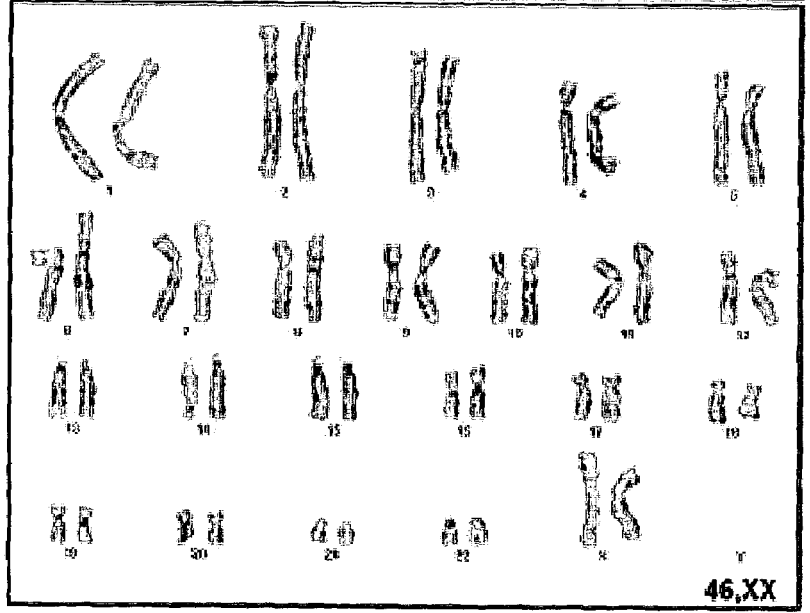

FIG. 3b illustrates karyotype analysis of the metaphase chromosomes shown in FIG. 3a. Karyotype was found to be 46, XX, which is a normal female, reflecting that the ES cells are free of foreskin cell contamination.

Figures 4A, 4B, 4C:
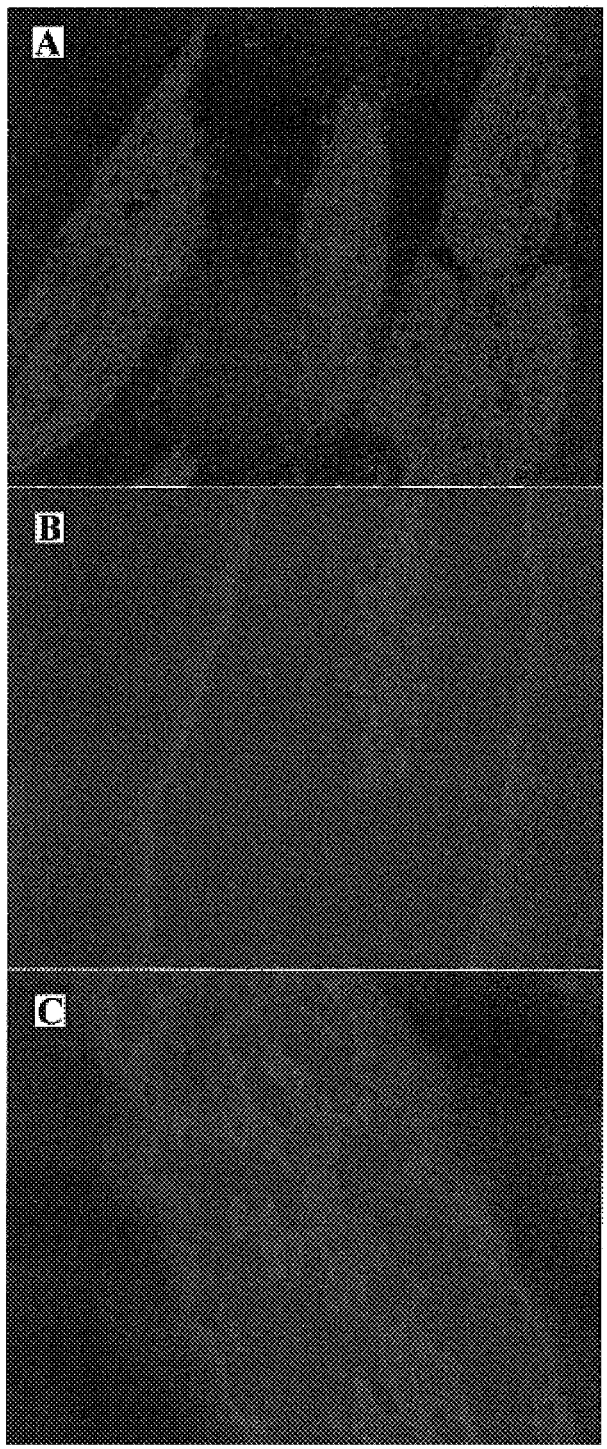

FIGS. 4a-c are immunohistochemistry micrographs illustrating the expression of embryonic cell surface markers on human ES cells following 57 passages on foreskin feeder layers. Shown are dark field images of human ES cells (line I-6) labeled with monoclonal antibodies specific to TRA-1-60 (FIG. 4a, 5× magnification), SSEA4 (FIG. 4b, 20× magnification) and TRA-1-81 (FIG. 4c, 20× magnification).

Figure 5:
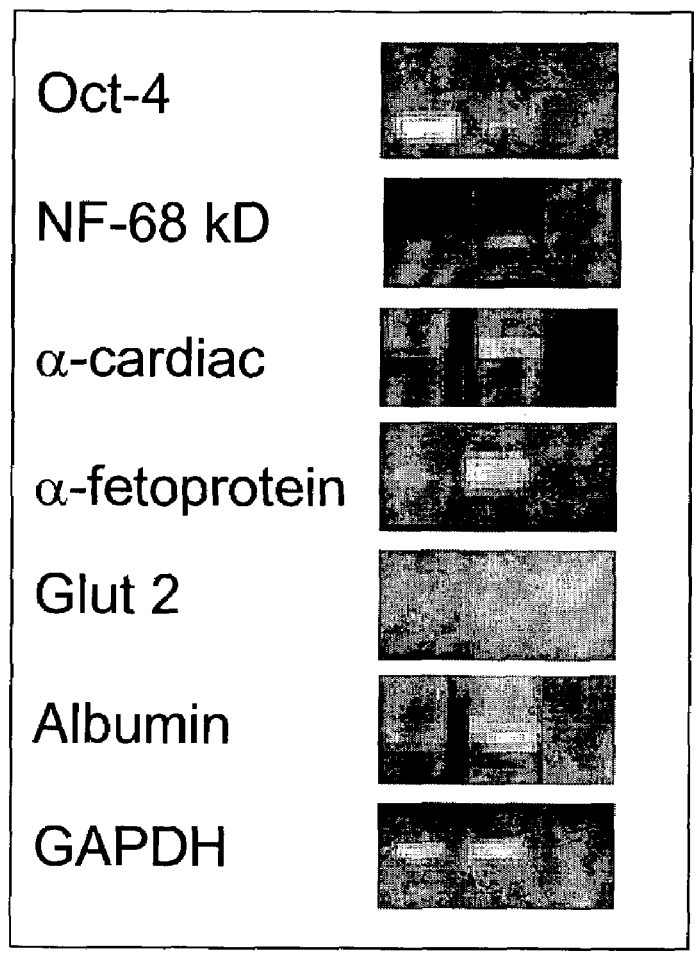

FIG. 5 illustrates the differentiation stage of two ES cell-lines (I-3 and I-6) grown on foreskin feeder layers (left lane) and in embryoid bodies (EBs) (right lane), as determined by RT-PCR. Equal loading and RNA concentration was verified by probing for expression of the housekeeping gene GAPDH.

Figures 6A, 6B:
Figures 6C, 6D:
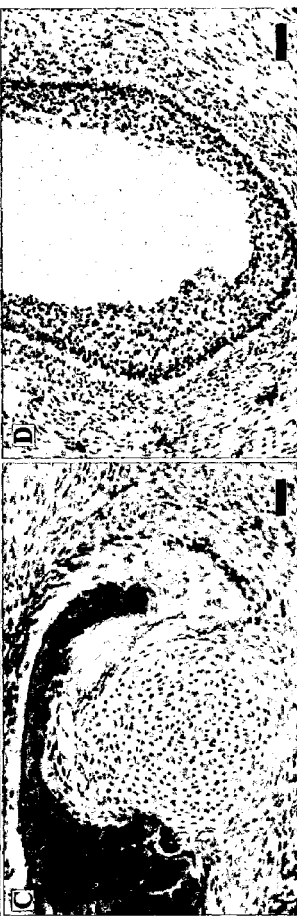
Figures 6E, 6F:
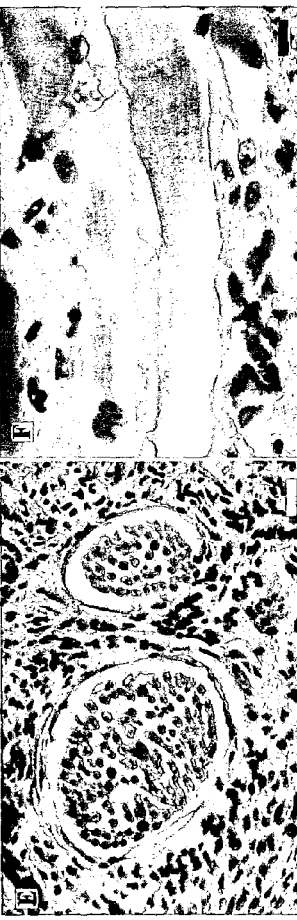

FIGS. 6a-f are photomicrographs illustrating in vivo differentiation to teratomas of human ES cells that have been grown on human foreskin feeder layers. Shown are hematoxyline-eosine stained sections of cartilage and mucus-secreting epithelium from I-3 ES cells following 20 passages on foreskin feeder layers (FIG. 6a, size bar represents 50 µM), epithelium with cells containing melanin from I-9 ES cells following 34 passages on foreskin feeder layers (FIG. 6b, size bar represents 25 µM), calcified cartilage tissue from I-3 ES cells following 20 passages on foreskin feeder layers (FIG. 6c, size bar represents 50 µM), stratified epithelium from I-3 ES cells following 20 passages on foreskin feeder layers (FIG. 6d, size bar represents 50 µM), transverse section of myelinated nerves from H-9 ES cells following 34 passages on foreskin feeder layers (FIG. 6e, size bar represents 25 µM), and developing striated muscle from I-6 ES cells following 50 passages on foreskin layers (FIG. 6f, size bar represents 10 µM).

DESCRIPTION OF THE PREFERRED EMBODIMENTS

The present invention is of human foreskin cells, which are capable of maintaining stem cells, such as human embryonic stem (ES) cells in an undifferentiated state.

The principles and operation of the feeder cells culture and the methods of co-culturing them with stem cells according to the present invention may be better understood with reference to the drawings and accompanying descriptions.

Before explaining at least one embodiment of the invention in detail, it is to be understood that the invention is not limited in its application to the details set forth in the following description or exemplified by the Examples. The invention is capable of other embodiments or of being practiced or carried out in various ways. Also, it is to be understood that the phraseology and terminology employed herein is for the purpose of description and should not be regarded as limiting.

Embryonic stem cells are derived from the inner cell mass (ICM) of the mammalian blastocyst. These cells are pluripotent, thus are capable of differentiating into a variety of somatic cell lineages (i.e., hematopoietic cells, neuronal cells, and cells of the immune system), thereby offering a unique source of cells which can be used in both research and clinical applications.

ES cells have been successfully established from primates (Thomson et al., 1998; Amit et al., 2000), mice (Mills and Bradley, 2001) and other species. Human ES cells are maintained in an undifferentiated pluripotent state when cultured under suitable conditions such as in the presence of a feeder layer or a matrix supplemented with serum or conditioned medium. However, therapeutic application of human ES cells requires defined growth conditions, pathogen-free environment and long culturing periods to enable proper characterization and genetic manipulation of the ES cells.

Current methods for culturing human ES cells are animal based, involving mouse embryonic fibroblasts (MEF) or mouse-derived matrices such as Matrigel®™ or laminin supplemented with MEF conditioned medium as feeder layers. Other, more advanced approaches involve the use of human based feeder cells such as human fallopian tube epithelial cells.

While the first are primarily limited by a laborious effort involved in the continuous preparation of fresh feeder layers and the undesired exposure of the human culture to xenogenic components which restrict their future use in therapy, the latter are limited by a shortened culturing period resulting in heterogeneous cultures.

While reducing the present invention to practice, the present inventors have uncovered that human foreskin cells are capable of sustaining human stem cells in culture while maintaining all ES cell features including pluripotency, immortality, undifferentiated proliferation capability and normal karyotype.

Previous attempts to culture human ES cells in the presence of a human feeder layer involved the use of human ES cells differentiated into fibroblast-like cells (U.S. Pat. Appl. No. 20020072117). It will be appreciated, however, that these feeder cells were initially grown on mouse embryonic fibroblasts, which may have introduced animal pathogens to the human ES culture. In addition, these human feeder cells are characterized by a relatively long doubling time and a limited culturing period of 7-10 passages which limits their use as a feeder layer.

In sharp contrast the human foreskin cells of the present invention provide an animal-free environment, are characterized by a short doubling time, culturing periods of at least 42 passages and as further described hereinunder are capable of maintaining ES cells in a pluripotent and undifferentiated state for at least 87 passages (see Example 1 of the Examples section which follows). As such, the human foreskin cells of the present invention provide for the first time a pathogen-free and homogeneous environment for culturing human ES cells.

Thus, according to one aspect of the present invention there is provided a cell culture comprising human foreskin cells, which are capable of maintaining stem cells in an undifferentiated state when co-cultured therewith.

As used herein, the phrase "stem cells" refers to cells which are capable of differentiating into other cell types having a particular, specialized function (i.e., "fully differentiated" cells) or remaining in an undifferentiated state hereinafter "pluripotent stem cells".

Non-limiting examples of stem cells are hematopoietic stem cells obtained from bone marrow tissue of an individual at any age or from cord blood of a newborn individual, embryonic stem (ES) cells obtained from the embryonic tissue formed after gestation (e.g., blastocyst), or embryonic germ (EG) cells obtained from the genital tissue of a fetus any time during gestation, preferably before 10 weeks of gestation. Further description of stem cells is provided hereinunder. Preferred stem cells according to this aspect of the present invention are human stem cells.

It will be appreciated that undifferentiated stem cells are of a distinct morphology, which is clearly distinguishable from differentiated cells of embryo or adult origin by the skilled in the art. Typically, undifferentiated stem cells have high nuclear/cytoplasmic ratios, prominent nucleoli and compact colony formation with poorly discernable cell junctions. Additional features of undifferentiated stem cells are further described hereinunder.

As described in Example 1 of the Examples section which follows, the human foreskin cells of the present invention are obtained from a human foreskin tissue (i.e., the skin tissue covering the glans penis; preputium penis) of a male individual, preferably from an 8-14 day old male individual. The foreskin tissue is first minced via scissors and then dissociated to single cells. Foreskin cell clamps can be dissociated by any means known in the art including physical de-clamping or enzymatic digestion using for example Trypsin.

Foreskin cells of the present invention are re-suspended in tissue culture medium supplemented with serum or serum-replacement. Serum can be of any source including fetal bovine serum, human serum or serum replacement. Preferably human serum or serum replacement is utilized in order to provide an animal-free environment for the foreskin feeder cells. Culture medium, serum, and serum replacement can be obtained from any commercial supplier of tissue culture products, examples include Gibco-Invitrogen Corporation (Grand Island, N.Y. USA), Sigma (St. Louis Mo., USA) and the ATCC (Manassas, Va. USA).

The serum or serum replacement used by the present invention for culturing the foreskin feeder cells is provided at a concentration range of 1% to 40%, more preferably, 5% to 35%, more preferably, 10% to 30%, most preferably 20% to 30%.

According to presently preferred embodiments of the present invention human serum is provided at a concentration of 20% and the serum replacement is provided at a concentration of 30% (see Example 1 of the Examples section).

As is illustrated in the Examples section which follows, the human foreskin feeder cells of the present invention are capable of forming monolayers when attached to a solid phase such as a tissue culture plate [Dugdale and Siddall (1969) J. Med. Lab. Technol. 26: 31-5]. This characteristic of the human foreskin feeder cells of the present invention makes these cells highly suitable for ES culturing since monolayers can be used as a feeder cell layer on which stem cells can proliferate while maintaining their undifferentiated features.

As used hereinbelow the phrase "feeder cell layer" refers to a cell monolayer usually from one tissue type which provides a surface suitable for the attachment and growth of cells (i.e., stem cells) from a second tissue type.

It will be appreciated that the human foreskin cells of the present invention can be modified (e.g., genetically) to include additional characteristics that provide a culturing advantage.

For example, the human foreskin cells can be genetically modified (transformed stably or transiently) to express drug resistance genes for one or more antibiotics or marker genes which may be used for immunoisolation. Examples of marker genes include, but are not limited to, green fluorescent protein, β-galactosidase and cell-surface antigens. As is further described in Example 1 of the Examples section which follows, the human foreskin of the present invention possess a natural resistance to at least one type of antibiotic, a feature which further enhances their applicability in culturing.

The human foreskin cells of the present invention can also be genetically modified to secrete factors which support growth of the stem cells in an undifferentiated state. Such factors include but are not limited to basic fibroblast growth factor (bFGF), members of the interleukin 6 (IL-6) and leukemia inhibitor factor (LIF) families of cytokines, and telomerase reverse transcriptase (TERT) at an elevated level (U.S. Pat. Appl. No. 20020072117 and WO 99/20741).

Genetic manipulation of the human foreskin cells of the present invention may be effected using molecular cloning and genetic engineering methods, which are well known to one skilled in the art.

Briefly, any of the genes described hereinabove or active portions thereof may be cloned into mammalian expression constructs containing promoter sequences enabling expression in foreskin cells such as the CMV promoter [Artuc et al., Exp. Dermatol. 1995, 4:317-21].

Examples of suitable constructs include, but are not limited to pcDNA3, pcDNA3.1 (+/−), pGL3, PzeoSV2 (+/−), pDisplay, pEF/myc/cyto, pCMV/myc/cyto each of which is commercially available from Invitrogen Co. (www.invitrogen.com), or the pSH expression vector which enables a regulated polynucleotide expression in human foreskin cells [Ventura and Villa, 1993, Biochem. Biophys. Commun. 192: 867-9]. Examples of retroviral vector and packaging systems are those sold by Clontech, San Diego, Calif., USA, including Retro-X vectors pLNCX and pLXSN, which permit cloning into multiple cloning sites and the transgene is transcribed from CMV promoter. Vectors derived from Mo-MuLV are also included such as pBabe, where the transgene will be transcribed from the 5'LTR promoter.

As is mentioned hereinabove and illustrated in the Examples section which follows, the human foreskin feeder cells of the present invention are capable of maintaining ES cells in an undifferentiated state when co-cultured therewith.

Thus, according to another aspect of the present invention there is provided a method of maintaining stem cells in an undifferentiated state. The method is effected by co-culturing the stem cells with the human foreskin cells of the present invention described hereinabove.

The stem cells can be obtained using well-known cell-culture methods. For example, human embryonic stem cells can be isolated from human blastocysts. Human blastocysts are typically obtained from human in vivo preimplantation embryos or from in vitro fertilized (IVF) embryos. Alternatively, a single cell human embryo can be expanded to the blastocyst stage. For the isolation of human ES cells the zona pellucida is removed from the blastocyst and the inner cell mass (ICM) is isolated by immunosurgery, in which the trophectoderm cells are lysed and removed from the intact ICM by gentle pipetting. The ICM is then plated in a tissue culture flask containing the appropriate medium which enables its outgrowth. Following 9 to 15 days, the ICM derived outgrowth is dissociated into clumps either by a mechanical dissociation or by an enzymatic degradation and the cells are then re-plated on a fresh tissue culture medium. Colonies demonstrating undifferentiated morphology are individually selected by micropipette, mechanically dissociated into clumps, and re-plated. Resulting ES cells are then routinely split every 1-2 weeks. For further details on methods of preparation human ES cells see Thomson et al., [U.S. Pat. No. 5,843,780; Science 282: 1145, 1998; Curr. Top. Dev. Biol. 38: 133, 1998; Proc. Natl. Acad. Sci. USA 92: 7844, 1995]; Bongso et al., [Hum Reprod 4: 706, 1989]; Gardner et al., [Fertil. Steril. 69: 84, 1998].

It will be appreciated that commercially available stem cells can be also be used with this aspect of the present invention. Human ES cells can be purchased from the NIH human embryonic stem cells registry (<http://escr.nih.gov>). Non-limiting examples of commercially available embryonic stem cell lines are BG01, BG02, BG03, BG04, CY12, CY30, CY92, CY10, TE03 and TE32.

Stem cells used by the present invention can be also derived from human embryonic germ (EG) cells. Human EG cells are prepared from the primordial germ cells obtained from human fetuses of about 8-11 weeks of gestation using laboratory techniques known to anyone skilled in the arts. The genital ridges are dissociated and cut into small chunks which are thereafter disaggregated into cells by mechanical dissociation. The EG cells are then grown in tissue culture flasks with the appropriate medium. The cells are cultured with daily replacement of medium until a cell morphology consistent with EG cells is observed, typically after 7-30 days or 1-4 passages. For additional details on methods of preparation human EG cells see Shamblott et al., [Proc. Natl. Acad. Sci. USA 95: 13726, 1998] and U.S. Pat. No. 6,090,622.

It will be appreciated that ES cells can be obtained from other species as well, including mouse (Mills and Bradley, 2001), golden hamster [Doetschman et al., 1988, Dev Biol. 127: 224-7], rat [Iannaccone et al., 1994, Dev Biol. 163: 288-92] rabbit [Giles et al. 1993, Mol Reprod Dev. 36: 130-8; Graves & Moreadith, 1993, Mol Reprod Dev. 1993, 36: 424-33], several domestic animal species [Notarianni et al., 1991, J Reprod Fertil Suppl. 43: 255-60; Wheeler 1994, Reprod Fertil Dev. 6: 563-8; Mitalipova et al., 2001, Cloning. 3: 59-67] and non-human primate species (Rhesus monkey and marmoset) [Thomson et al., 1995, Proc Natl Acad Sci USA. 92: 7844-8; Thomson et al., 1996, Biol Reprod. 55: 254-9].

Once obtained, stem cells are co-cultured with the human foreskin cells of the present invention. Co-culturing may be effected using any culture medium, serum or serum replacement including the examples provided hereinabove. Preferably, culture medium is supplemented with factors which promote stem cell growth. Examples includes but are not limited to amino acids, growth factors such as those described hereinabove, antibiotics and the like.

Stem cells are plated onto the foreskin cells in a density which promotes cell survival and proliferation but limits differentiation. Typically, a plating density of between about 15,000 cells/cm$^2$ and about 50,000 cells/cm$^2$ is used.

It will be appreciated that although single-cell suspensions of stem cells are usually seeded, small clusters may also be used. To this end enzymatic digestion is terminated before stem cells become completely dispersed and the cells are triturated with a pipette such that clumps (i.e., 10-200 cells) are formed. However, measures are taken to avoid large clusters which cause cell differentiation.

Preferably, the human foreskin cells of the present invention are growth suppressed by irradiation or treatment with an anti-mitotic agent such as mitomycin C, to prevent them from outgrowing the stem cells.

When co-cultured, stem cell growth is monitored to determine their differentiation state. Several approaches, including, for example, morphological determination can be used to determine cellular differentiation. As described hereinabove, a number of morphological features characterize undifferentiated stem cells. These include high nuclear/cytoplasmic ratios, prominent nucleoli and compact colony formation with poorly discernable cell junctions (see Example 1 of the Examples section).

Alternatively, cell differentiation can be determined upon examination of cell or tissue-specific markers which are known to be indicative of differentiation. For example, primate ES cells may express one or more stage-specific embryonic antigens (SSEA) 3 and 4 as shown in Example 2 of the Examples section which follows. Differentiation of human ES cells in vitro results in the loss of these markers and increased expression of others such as α-fetoprotein, NF-68 kDa, α-cardiac, Glut 2 and albumin as shown in Example 3 of the Examples section which follows.

Tissue/cell specific markers can be detected using immunological techniques known in the art (Thomson et al., 1998). Examples include but are not limited to flow cytometry for membrane-bound markers, immunohistochemistry for extracellular and intracellular markers and enzymatic immunoassay, for secreted molecular markers.

Differentiation markers can also be detected at the mRNA level such as by reverse transcriptase-PCR using marker-specific primers (see Example 3 of the Examples section). For example, Oct-4 and TERT can be detected by RT-PCR.

Another approach to determine ES cell differentiation is effected via measurements of alkaline phosphatase activity. Undifferentiated human ES cells have alkaline phosphatase activity, which can be detected by fixing the cells with 4% paraformaldehyde and developing with the Vector Red substrate kit according to manufacturer's instructions (Vector Laboratories, Burlingame, Calif., USA).

The ability of ES cells to differentiate into cells of all three germinal levels (i.e., pluripotency) can also be used to monitor ES cell differentiation. Pluripotency of ES cells can be confirmed by injecting cells into SCID mice [Evans M J and Kaufman M (1983). Pluripotential cells grown directly from normal mouse embryos. Cancer Surv. 2: 185-208], which upon injection form teratomas. Teratomas are fixed using 4% paraformaldehyde and histologically examined for the three germ layers (i.e., endoderm, mesoderm and ectoderm). Alternatively, pluripotency of the stem cells of the present invention can be determined by their ability to form embryonal bodies as described in Example 3 of the Examples section which follows.

In addition to monitoring a differentiation state, stem cells are often also monitored for karyotype, in order to verify cytological euploidity, wherein all chromosomes are present and not detectably altered during culturing. Cultured stem cells can be karyotyped using a standard Giemsa staining and compared to published karyotypes of the corresponding species.

As is illustrated in Example 2 of the Examples section below, stem cells cultured according to the teachings of this aspect of the present invention retain a normal karyotype following 47 passages on foreskin feeder cells substantiating the ability of the present culturing methodology to support growth of stem cells in culture.

Co-culturing by the present invention may also be effected by growing of the stem cells on a synthetic matrix supplemented with a foreskin-derived conditioned medium.

A human foreskin cell conditioned medium refers to a medium enriched with foreskin secreted factors present in the foreskin culture following a certain culturing period, which factors are sufficient to maintain stem cells in culture.

The synthetic matrix can substitute the need for feeder cells since it contains extracellular components to which the stem cells can attach and provides a suitable culture substrate.

Particularly suitable are extracellular matrix components, such as those derived from basement membrane or that may form part of adhesion molecule receptor-ligand couplings. A commercial preparation is available from Becton Dickenson under the name Matrigel®™, and can be obtained in a Growth Factor Reduced formulation. Both formulations are effective. Matrigel®™ is a soluble preparation from Engelbreth-Holm-Swarm tumor cells that gels at room temperature to form a reconstituted basement membrane. Other extracellular matrix components and component mixtures are suitable as an alternative. Depending on the cell type being proliferated, this may include laminin, fibronectin, proteoglycan, entactin, heparan sulfate, and the like, alone or in various combinations. Preferably recombinant extracellular matrix proteins are used for culturing human stem cells.

The human foreskin cell conditioned medium is produced by culturing human foreskin cells in a growth medium under conditions suitable for producing the conditioned medium.

The growth medium may be any growth medium suitable for growing the foreskin cells of the present invention, as described hereinabove. The growth medium may be supplemented with nutritional factors, such as amino acids, (e.g., L-glutamine), anti-oxidants (e.g., beta-mercaptoethanol) and growth factors, which benefit stem cell growth in an undifferentiated state. Serum and serum replacements are added at the hereinabove described effective concentration ranges.

Cells are cultured in the growth medium for sufficient time to allow adequate accumulation of secreted factors to support stem cell proliferation in an undifferentiated state. Typically, the medium is conditioned by culturing for 24 hours at 37° C. However, the culturing period can be scaled by assessing the effect of the conditioned medium on stem cell growth and differentiation (as described hereinabove and in Example 1). According to presently known embodiments of this aspect of the present invention the medium is conditioned for 4 hours.

Selection of culture apparatus for conditioning the medium is based on the scale and purpose of the conditioned medium. Large scale production preferably involves the use of dedicated devices. Continuous cell culture systems are reviewed in Furey (2000) Genetic Eng. News 20:10.

Following accumulation of adequate factors in the medium, growth medium (i.e., conditioned medium) is separated from the human foreskin cells and collected. It will be appreciated that the human foreskin cells can be used repeatedly to condition further batches of medium over additional culture periods, provided that the cells retain their ability to condition the medium.

Preferably, the conditioned medium is sterile filtrated prior to use. The conditioned medium of the present invention may be applied directly on stem cells or extracted to concentrate the effective factor such as by salt filtration. For future use, conditioned medium is preferably stored frozen at −80° C.

The ability of the conditioned medium of the present invention to maintain stem cells in an undifferentiated state is assessed as described hereinabove.

As described hereinbelow and in Example 1 of the Examples section which follows, the novel foreskin-derived feeder cells of the present invention provide an excellent substitute to prior art feeder cells since they can be maintained in culture for long periods of times of at least 42 passages (ATCC Catalogue) and provide a complete pathogen-free environment for culturing the stem cells. When cultured for a long period of time on a constant, pathogen-free feeder layer, the human ES cells become more attractive for clinical research and human therapy.

The human ES cells cultured according to the teachings of the present invention can be used for several commercial and research applications.

Cultured human ES cells can be differentiated into restricted developmental lineage cells, or terminally differentiated cells. Differentiation of stem cells can be initiated by allowing overgrowth of undifferentiated human ES cells in suspension culture forming embryoid bodies or by plating ES cells under conditions that promote differentiation in a particular manner. Such conditions may include withdrawing or adding nutrients, growth factors or cytokines to the medium, changing the oxygen pressure, or altering the substrate on the culture surface.

Cultured human ES cells obtained by the present invention can be also used to prepare a cDNA library relatively uncontaminated with cDNA from feeder cells. mRNA is prepared by standard techniques from the ES cells and is further reverse transcribed to form cDNA. The cDNA preparation can be subtracted with nucleotides from embryonic fibroblasts and other cells of undesired specificity, to produce a subtracted cDNA library by techniques known in the art.

Human ES cells cultured according to the teachings of the present invention can be used to screen for factors (such as small molecule drugs, peptides, polynucleotides, and the like) or conditions (such as culture conditions or manipulation) that affect the characteristics of stem cells. For example, growth affecting substances, toxins or potential differentiation factors can be tested by their addition to the culture medium.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Reference is now made to the following examples, which together with the above descriptions, illustrate the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Culture of Animal Cells—A Manual of Basic Technique" by Freshney, Wiley-Liss, N.Y. (1994), Third Edition; "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorpotaed by reference as if fully set forth herein. Other general references are provided throughout this document. The procedures therein are believed to be well known in the art and are provided for the convenience of the reader. All the information contained therein is incorporated herein by reference.

Example 1

Foreskin—Derived Cell Lines Suitable for Growing ES Cells

Materials and Experimental Methods

Establishment of foreskin feeder cell lines—Foreskin tissue was obtained by parental informed consent from 8 to 14 day old normal males. Tissue was washed in sterile PBS (Invitrogen, Grand island, N.Y., USA), minced via scissors and dissociated to single cells by incubation with Trypsin-EDTA (0.5% Trypsin, 5.3 mM EDTA, Invitrogen, Grand Island, N.Y., USA) for 20-40 min. Resulting single cell suspensions were grown in a culture medium including 80% Dulbecco's modified Eagle's medium (DMEM) containing high glucose concentration and no pyruvate (Invitrogen, Grand island, N.Y., USA), 2 mM L-glutamine, 0.1 mM β-mercaptoethanol, and 1% non-essential amino acid stock (all purchased from Invitrogen, Grand island, N.Y., USA products). Foreskin medium was supplemented with serum or serum replacement as follows: Growth medium for foreskin cell lines F3, F7 and F8 was supplemented with 20% fetal bovine serum (FBS) (Hyclone, Logan, Utah, USA), growth medium for foreskin cell lines F2, F4 and F6 was supplemented with 30% serum replacement (SR) (Invitrogen, Grand island, N.Y., USA), and growth medium for foreskin cell lines F1, F5 and F9 was supplemented with 20% human serum (Chemicon Intnl, Inc. Temecula, Calif., USA). The foreskin cells were split using Trypsin-EDTA (0.5% trypsin 0.25% EDTA, Invitrogen, Grand island, N.Y., USA) for 8 min every five to seven days. Prior to use, foreskin cells were mitotically inactivated by incubating cells with 10 ng/ml mitomycin C (Sigma, St. Louis Mo., USA) for two hours followed by 4 washes in PBS. Cells were then collected with Trypsin-EDTA (0.5% Trypsin 0.25% EDTA) by incubating for 8 min, centrifuged at 1500 RPM for 5 min, resuspended in feeder medium, and plated at a concentration of 40,000 cells per $cm^2$.

ES cell lines—The previously described human ES cell lines I-6, I-3 (Amit and Itskovitz-Eldor, 2002) and H-9 (Thomson et al, 1998) were collected using 1 mg/ml Type IV Collagenase (Invitrogen, Grand island, N.Y., USA) and transferred into 2 ml wells in 6-well plates containing pre-plated foreskin cells. Co-cultures were grown in a medium consisting of 85% Ko-DMEM, supplemented with 15% SR, 1 mM L-glutamine, 0.1 mM β-mercaptoethanol, 1% non-essential amino acid stock, and 4 ng/ml bFGF (all purchased from Invitrogen, Grand island, N.Y., USA). Adherent co-cultures were split every four to six days using 1 mg/ml Type IV Collagenase for 30 min and re-plated in flasks containing fresh medium.

Morphological assessment—ES cells were examined under an inverted scope (live cells), using phase contrast (Olympus, IX70, Japan).

Experimental Results

Foreskin-derived cell lines provide excellent feeder layers for ES cell growth—In order to establish an animal-free environment for the growth of human embryonic stem cells foreskin cell lines have been generated as feeder layers.

Foreskin cells grown in medium supplemented with FBS gave rise to fibroblast-like cell lines, which persisted for more than 27 consecutive passages. No reduction in the foreskin cell growth rate or in its ability to support human ES cell growth was observed regardless of whether foreskin cells used were of a high passage number, or following freeze and thaw cycles. Noteworthy is that when in culture, foreskin fibroblasts have been reported to grow at least 42 passages prior to senescence (ATCC Catalogue). Similarly, the growth rate and morphology of foreskin cell lines derived using SR or human serum (F1, F2, F4, F5, F6 and F9), paralleled that of lines derived with FBS.

To determine the ability of human foreskin cells to support growth of human ES cells, the two cell populations were co-cultured in 85% Ko-DMEM supplemented with 15% SR as detailed in Methods hereinabove. Human ES lines, I-3, I-6 and H-9 initially grown on MEF supplemented with SR responded well to transfer to foreskin feeder layers. Each transferred line continued proliferation and maintained normal ES cell features for at least 70 passages. The morphology of the ES colonies grown on foreskin feeder layers slightly differed from that of cells grown on MEF. When grown on foreskin feeders ES cell growth was organized according to the direction of growth of the foreskin layers (FIG. 1a) resulting in somewhat less round colonies (data not shown). However, when viewed under a higher magnification the foreskin derived ES cell morphology was identical to that of the MEF derived ES cells. Essentially, ES cells remained round and small, with a high nucleus to cytoplasm ratio with notable presence of one to three nucleoli and typical spacing between the cells (FIG. 1b). In addition, human ES lines grown initially on one of the foreskin lines for 20 passages, following which, ES cells were grown on another foreskin line, revealed no difference in ES cell growth. Each of F3, F7, F8, F1, F5, F4 and F2 foreskin lines supported equally human ES cell growth, and substituted for each other, mid-culture (from 5 to more than 20), as feeders for ES cells. Following 76 passages of mid-culture substitutions, ES cells were transferred to a pathogen-free environment supplied by each of the animal-free foreskin lines (i.e., F1, F2, F4, F5, F6 and F9). Under these conditions ES cells were propagated and maintained pluripotent and in an undifferentiated state for at least 11 passages.

These results demonstrate the ability of foreskin feeder cells of the present invention to support a normal growth of human ES cells and substitute MEF as feeder layers.

Foreskin feeder cell lines are characterized by a natural resistance to antibiotic—For post-transfectional antibiotic selection hES cells are usually grown on transgenic MEFs demonstrating Neomycin resistance at a concentration of 200 ng/ml [Eiges et al., (2001). Current Biology 11: 514-518]. To test their antibiotic resistance unmodified human F-3 foreskin and MEF cell lines were grown in a medium supplemented with 100 μg/ml of Neomycin. While the MEF cells started to die on the second day following Neomycin selection and demonstrated an aberrant phenotype (FIG. 2a), the human foreskin cells appeared phenotypically normal and competent for hES plating without any detectable cell death even following 4 days of antibiotic selection (FIG. 2b).

These results demonstrate that foreskin cells have a natural resistance to antibiotic which can be utilized for post-transfectional antibiotic selection of human ES cells.

Example 2

Foreskin-Derived Feeder Cell Lines Support Growth of Phenotypically Consistent ES Cells Materials and Experimental Methods Karyotype analysis—ES cells metaphases were blocked using colcemid (KaryoMax colcemid solution, Invitrogen, Grand island, N.Y., USA) and nuclear membranes were lysed in an hypotonic solution according to standard protocols (International System for Human Cytogenetic Nomenclature, ISCN). G-banding of chromosomes was performed according to manufacturer's instructions (Giemsa, Merck). Karyotypes of at least 50 cells per sample were analyzed and reported according to the ISCN.

Immunohistochemistry—Cells were fixed for 20 min in 4% paraformaldehyde, blocked for 15 min in 2% normal goat serum in PBS (Biological Industries, Beth Haemek, Israel) and incubated for overnight at 4° C. with 1:50 dilutions of SSEA1, SSEA3, SSEA4, TRA-60, TRA-81 mouse anti-human antibodies, provided by Prof. P Andrews the University of Sheffield, England. Cells were then washed in PBS and further incubated with 1:100 dilutions of Donkey anti-mouse IgG antibodies conjugated to the fluorochrome Cys 3 (Chemicon International, Temecula Calif., USA). Cells were visualized under an inverted fluorescent microscope (CARL Zeiss, Germany).

Experimental Results

Foreskin-derived feeder cell lines provide ES cells with consistent karyotype and phenotype as other feeder cell growth protocols—To test the ability of foreskin feeder layers to support normal growth of ES cells, karyotype analysis was performed on ES cells following continuous culturing on foreskin feeder layers.

Two separate batches of I-3 and one of H-9 ES cell lines were tested following 22, 29 or 47 passages.

As shown in FIG. 3, all tested metaphase-blocked ES cells exhibited normal karyotype (i.e., 46, XX). These results demonstrate that foreskin feeder cells are able to maintain human ES cells with stable chromosomes for long culturing periods.

Human ES cells co-cultured with foreskin-derived feeder cells express embryonic surface markers—In order to further characterize the ability of foreskin derived feeder cells to maintain normal growth of human ES cells, IHC was performed on human ES cells with embryonic surface marker antibodies including TRA-1-60, SSEA4, TRA-1-81, SSEA3 and SSEA1.

Following 57 passages on foreskin derived feeder layers, the I-6 human ES cells demonstrated high expression levels of TRA-1-60, SSEA4 and TRA-1-81 (FIGS. 4a, b and c, respectively). These markers are typical characteristics of undifferentiated ES cells (Thomson et al., 1998, 1996, 1995). Notably, the stage-specific embryonic antigen 3 (SSEA3) was only moderately expressed while expression of the stage-specific embryonic antigen 1 (SSEA1), a unique marker of mouse ES cells, was not detected (data not shown).

These results demonstrate that foreskin derived feeder cells are able to maintain human ES cells in an undifferentiated state after a prolonged culturing period.

Example 3

Foreskin-Derived Feeder Cells Support Growth of Functional ES Cells

Materials and Experimental Methods:

Formation of embryoid bodies (EBs) from human ES cells—Human ES cells grown on foreskin derived feeder layers were removed from the 6-well plate (60 cm$^2$) co-culture by Type IV Collagenase (1 mg/ml) and were further dissociated into small clamps using 1000 μl Gilson pipette tips. Thereafter, dissociated cells were cultured in 58 mm Petri dishes (Greiner, Germany) in a medium consisting of 80% Ko-DMEM, supplemented with 20% fetal bovine serum defined (FBSd, HyClone, Utah, USA), 1 mM L-glutamine, 0.1 mM β-mercaptoethanol, and 1% non-essential amino acid stock. Unless otherwise noted all were purchased from Gibco Invitrogen corporation, USA. Formation of EBs was examined following one month in suspension.

Reverse transcriptase (RT) coupled PCR—Total RNA was isolated from either undifferentiated human ES cells or from one-month-old EBs using Tri-Reagent kit (Sigma-Aldrich Corp., St Louis, Mo., USA), according to the manufacturer's protocol. cDNA synthesis was performed on 1 μg total RNA template using MMLV RT (Promega Corp., Madison, Wis., USA) according to manufacturer's instructions. PCR primers and reaction conditions are described in Table 1, hereinbelow. All PCR reactions included an initial strand denaturation for 5 minutes at 94° C. PCR products were size-fractionated using 2% agarose gel electrophoresis.

cells are functionally, as well as phenotypically consistent with human ES cells derived by other feeder cell protocols the ES cells were removed from the co-cultures of the present invention and were grown in suspension. As a result, embryoid bodies (EBs) were isolated, and ES-consistent gene expression within the EBs was verified using RT-PCR. Within the EBs stem cells differentiated into representative cells of the three embryonic germ layers i.e., mesoderm, endoderm and ectoderm. As shown in FIG. 5, while undifferentiated cells grown on foreskin-derived feeder lines expressed Oct 4, a marker for pluripotent embryonic stem and germ cells [Pesce M, and Scholer H R. Oct-4: gatekeeper in the beginnings of mammalian development (2001). Stem Cells 19(4): 271-8], cells harvested from one-month-old EBs expressed genes, which are associated with cellular differentiation including neurofilament (NF-68 kD) related with embryonal ectoderm, α-cardiac associated with embryonal mesoderm, and α-fetoprotein, Glut 2 and albumin all of being indicators of embryonal endoderm. The diminished Oct 4 expression in EBs samples was consistent with previous reports of diminished Oct 4 expression following differentiation of totipotent cells to somatic lineages (Thomson et al., 1998, Reubinoff et al., 2000).

Thus, these results demonstrate that human ES cells grown on foreskin derived feeder cells are capable of creating functional EBs with cells that are differentiated to the various somatic lineages.

ES cells co-cultured with foreskin-derived feeder cells differentiate into embryonic germ layers in vivo—To further substantiate the ability of foreskin lines supported human ES cells to differentiate to embryonal germ layers, ES cells were tested for teratoma formation in vivo. Following injection to SCID beige mice, the three ES cell lines, I-3, H-9 and I-6 were able to form teratomas. Each teratoma contained

TABLE 1

| Gene product (Accession number) | SEQ ID NOs. | Forward (F) and reverse (R) primers (5'→3') | Reaction Condition | Size (bp) |
|---|---|---|---|---|
| Oct-4 (S81255) | SEQ ID NO: 1<br>SEQ ID NO: 2 | F: GAGAACAATGAGAACCTTCAGGA<br>R: TTCTGGCGCCGGTTACAGAACCA | 30 cycles at 60° C. in 1.5 mM MgCl$_2$ | 219 |
| NF-68 kD (AY156690) | SEQ ID NO: 3<br>SEQ ID NO: 4 | F: GAGTGAAATGGCACGATACCTA<br>R: TTTCCTCTCCTTCTTCACCTTC | 30 cycles at 60° C. in 2 mM MgCl$_2$ | 473 |
| α-cardiac actin (NM_005159) | SEQ ID NO: 5<br>SEQ ID NO: 6 | F: GGAGTTATGGTGGGTATGGGTC<br>R: AGTGGTGACAAAGGAGTAGCCA | 35 cycles at 65° C. in 2 mM MgCl$_2$ | 486 |
| α-fetoprotein (BC027881) | SEQ ID NO: 7<br>SEQ ID NO: 8 | F: GCTGGATTGTCTGCAGGATGGGAA<br>R: TCCCCTGAAGAAAATTGGTTAAAAT | 30 cycles at 60° C. in 1.5 mM MgCl$_2$ | 216 |
| Glut 2 (J03810) | SEQ ID NO: 9<br>SEQ ID NO: 10 | F: AGGACTTCTGTGGACCTTATGTG<br>R: GTTCATGTCAAAAAGCAGGG | 35 cycles at 55° C. in 1.5 mM MgCl$_2$ | 231 |
| Albumin (AF542069) | SEQ ID NO: 11<br>SEQ ID NO: 12 | F: TGCTTGAATGTGCTGATGACAGGG<br>R: AAGGCAAGTCAGCAGCCATCTCAT | 35 cycles at 60° C. in 1.5 mM MgCl$_2$ | 302 |
| GAPDH (J04038) | SEQ ID NO: 13<br>SEQ ID NO: 14 | F: AGCCACATCGCTCAGACACC<br>R: GTACTCAGCGCCAGCATCG | 30 cycles at 60° C. in 1.5 mM MgCl$_2$ | 302 |

Teratomas formation—ES cells co-cultured for at least 20 passages with foreskin derived feeder cells were drawn from 4-6 confluent 10 cm$^2$ plates. Cells were then injected into the rear leg muscle of 4-week-old male SCID-beige mice (Harlan, Jerusalem Israel). Resulting teratomas were examined histologically, at least 10 weeks post-injection.

Experimental Results

ES cells spontaneously differentiate into embryonic germ layer cell types in vitro, following their removal from foreskin-derived feeder cell co-cultures—To verify that human ES cells co-cultured with foreskin-derived feeder representative tissues of the three embryonic germ layers, including cartilage tissue, smooth muscle, stratified epithelium, melanin secreting cells, connective tissue and gut-like epithelium. Representative tissues formed in these teratomas are demonstrated in FIG. 6.

In conclusion, human ES cells grown on foreskin-derived feeder cells were thus functionally indistinct from cells grown with alternate protocols. Following differentiation, ES cells expressed genes associated with all three embryonal germ layers, in vitro, and formed teratomas in vivo, consisting of tissue arising from all three germ layers, as well.

Unlike other protocols, however, ES cells were propagated in culture for extended periods of time currently as many as 87 passages, maintaining their pluripotent, undifferentiated state.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

REFERENCES CITED (Additional References are Cited in the Text)

1. Amit M, Carpenter M K, Inokuma M S, Chiu C P, Harris C P, Waknitz M A, Itskovitz-Eldor J, Thomson J A. (2000). Clonally derived human embryonic stem cell lines maintain pluripotency and proliferative potential for prolonged periods of culture. Dev. Biol. 227: 271-8.
2. Amit M and Itskovitz-Eldor J. (2002). Derivation and spontaneous differentiation of human embryonic stem cells. J Anat 200: 225.
3. Evans M J, Kaufman M H. (1981). Establishment in culture of pluripotential cells from mouse embryos. Nature 292: 154-6.
4. Martin G R. (1981). Isolation of a pluripotent cell line from early mouse embryos cultured in medium conditioned by teratocarcinoma stem cells. Proc Natl Acad Sci USA 78: 7634-8.
5. Mills A A and Bradley A (2001). From mouse to man: generating megabase chromosome rearrangements. Trends Genet. 17: 331-9.
6. Reubinoff B E, Pera M F, Fong C, Trounson A, Bongso A. (2000). Embryonic stem cell lines from human blastocysts: somatic differentiation in vitro. Nat. Biotechnol. 18: 399-404.
7. Richards M, Fong C Y, Chan W K, Wong P C, Bongso A. (2002). Human feeders support prolonged undifferentiated growth of human inner cell masses and embryonic stem cells. Nat. Biotechnol. 20: 933-6.
8. Thomson J A, Itskovitz-Eldor J, Shapiro S S, Waknitz M A, Swiergiel J J, Marshall V S, Jones J M. (1998). Embryonic stem cell lines derived from human blastocysts. Science 282: 1145-7 [erratum in Science 1998;282: 1827].
9. Thomson J A, Kalishman J, Golos T G, Durning M, Harris C P, Hearn J P. (1996). Pluripotent cell lines derived from common marmoset (Callithrix jacchus) blastocysts. Biol Reprod 55: 254-9.
10. Thomson J A, Kalishman J, Golos T G, Durning M, Harris C P, Becker R A, Hearn J P. (1995). Isolation of a primate embryonic stem cell line. Proc Natl Acad Sci USA 92: 7844-8.

What is claimed is:

1. A method of maintaining embryonic stem cells in an undifferentiated state comprising co-culturing the embryonic stem cells with a human foreskin fibroblast feeder cell line.

2. The method of claim 1, wherein said human foreskin fibroblast feeder cell line is prepared by:
   (a) isolating foreskin cells from foreskin tissue;
   (b) culturing said foreskin cells in a culture medium including serum and/or serum replacement thereby preparing said human foreskin fibroblast feeder cell line.

3. The method of claim 1, wherein said embryonic stem cells are of human origin.

4. The method of claim 2, wherein said foreskin tissue is obtained from an 8-14 day old male individual.

5. The method of claim 2, wherein step (a) is effected by:
   (i) mincing said foreskin tissue;
   (ii) dissociating said foreskin tissue resultant from step (i) into single cells.

6. The method of claim 5, wherein step (ii) is effected via treatment with trypsin.

7. The method of claim 2, wherein said serum and/or said serum replacement are provided at a concentration of at least 10%.

8. The method of claim 2, wherein said serum is human serum.

9. The method of claim 2, wherein said serum and/or said serum replacement are provided at a concentration of 15%.

10. A cell culture comprising:
    (i) embrynoic stem cells; and
    (ii) human foreskin fibroblast cells capable of maintaining said embryonic stem cells in an undifferentiated state.

11. The cell culture of claim 10, wherein said embryonic stem cells are of human origin.

12. The cell culture of claim 10, wherein said human foreskin fibroblast cells are capable of forming a mono-layer in the cell culture.

13. The cell culture of claim 10, wherein said cell culture includes a culture medium including serum replacement and/or human serum.

14. The cell culture of claim 13, wherein said serum replacement and/or said human serum are provided at a concentration of at least 10%.

15. The cell culture of claim 13, wherein said serum replacement and/or said human serum are provided at a concentration of 15%.

16. The cell culture of claim 10, wherein said human foreskin fibroblast cells of said cell culture maintain said embryonic stem cells in an undifferentiated, proliferative state through at least 87 passages.

* * * * *

SEQUENCE LISTING

```
<160> NUMBER OF SEQ ID NOS: 14

<210> SEQ ID NO 1
<211> LENGTH: 23
<212> TYPE: DNA
<213> ORGANISM: Artificial sequence
<220> FEATURE:
<223> OTHER INFORMATION: Single strand DNA oligonucleotide

<400> SEQUENCE: 1
gagaacaatg agaaccttca gga                                              23

<210> SEQ ID NO 2
<211> LENGTH: 23
<212> TYPE: DNA
<213> ORGANISM: Artificial sequence
<220> FEATURE:
<223> OTHER INFORMATION: Single strand DNA oligonucleotide

<400> SEQUENCE: 2
ttctggcgcc ggttacagaa cca                                              23

<210> SEQ ID NO 3
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 3
```
gagtgaaatg gcacgatacc ta                                         22

<210> SEQ ID NO 4
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 4
tttcctctcc ttcttcacct tc                                         22

<210> SEQ ID NO 5
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 5
ggagttatgg tgggtatggg tc                                         22

<210> SEQ ID NO 6
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 6
agtggtgaca aaggagtagc ca                                         22

<210> SEQ ID NO 7
<211> LENGTH: 25
<212> TYPE: DNA
<213> ORGANISM: Artificial sequence
<220> FEATURE:
<223> OTHER INFORMATION: Single strand DNA oligonucleotide

<400> SEQUENCE: 7
gctggattgt ctgcaggatg gggaa                                      25

<210> SEQ ID NO 8
<211> LENGTH: 25
<212> TYPE: DNA
<213> ORGANISM: Artificial sequence
<220> FEATURE:
<223> OTHER INFORMATION: Single strand DNA oligonucleotide

<400> SEQUENCE: 8
tcccctgaag aaaattggtt aaaat                                      25

<210> SEQ ID NO 9
<211> LENGTH: 23
<212> TYPE: DNA
<213> ORGANISM: Artificial sequence
<220> FEATURE:
<223> OTHER INFORMATION: Single strand DNA oligonucleotide

<400> SEQUENCE: 9
aggacttctg tggaccttat gtg                                        23

<210> SEQ ID NO 10
<211> LENGTH: 20
<212> TYPE: DNA
<213> ORGANISM: Artificial sequence -continued

```
<220> FEATURE:
<223> OTHER INFORMATION: Single strand DNA oligonucleotide

<400> SEQUENCE: 10
gttcatgtca aaaagcaggg                                                      20

<210> SEQ ID NO 11
<211> LENGTH: 24
<212> TYPE: DNA
<213> ORGANISM: Artificial sequence
<220> FEATURE:
<223> OTHER INFORMATION: Single strand DNA oligonucleotide

<400> SEQUENCE: 11
tgcttgaatg tgctgatgac aggg                                                 24

<210> SEQ ID NO 12
<211> LENGTH: 24
<212> TYPE: DNA
<213> ORGANISM: Artificial sequence
<220> FEATURE:
<223> OTHER INFORMATION: Single strand DNA oligonucleotide

<400> SEQUENCE: 12
aaggcaagtc agcagccatc tcat                                                 24

<210> SEQ ID NO 13
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 13
agccacatcg ctcagacacc                                                      20

<210> SEQ ID NO 14
<211> LENGTH: 19
<212> TYPE: DNA
<213> ORGANISM: Artificial sequence
<220> FEATURE:
<223> OTHER INFORMATION: Single strand DNA oligonucleotide

<400> SEQUENCE: 14
gtactcagcg ccagcatcg                                                       19
```